United States Patent [19]

Meinke et al.

[11] Patent Number: 5,244,879
[45] Date of Patent: Sep. 14, 1993

[54] 23-NOR-23-OXA AVERMECTIN ANALOGS ARE ACTIVE ANTHELMINTIC AGENTS

[75] Inventors: Peter T. Meinke, New York, N.Y.; Helmut Mrozik, Matawan, N.J.

[73] Assignee: Merck & Co., Inc., Rahway, N.J.

[21] Appl. No.: 853,452

[22] Filed: Mar. 18, 1992

[51] Int. Cl.$^5$ .................... A61K 31/71; A61K 31/365
[52] U.S. Cl. ...................................... 514/30; 514/450; 536/7.1; 549/264
[58] Field of Search ................... 549/264; 514/450, 30; 536/7.1

[56] References Cited

U.S. PATENT DOCUMENTS 4,199,569  4/1980  Chabala et al. ............... 549/264
4,310,519  1/1982  Albers-Schonberg et al. ...... 536/7.1

Primary Examiner—Alan L. Rotman
Assistant Examiner—A. A. Owens
Attorney, Agent, or Firm—David L. Rose; Joseph F. DiPrima

[57] ABSTRACT

Avermectin analogs are prepared where the 23-position ring carbon atom is deleted and replaced by an oxygen atom. The compounds are prepared by opening the outer spiroketal ring to gain access to the 23-position atom, substituting the ring-opened compounds with a substituent containing the oxygen atom in the appropriate position and closing the ring to prepare the desired compounds. The compounds are potent anthelmintic agents and methods and compositions including such 23-nor-23-oxa compounds are also disclosed.

8 Claims, No Drawings

23-NOR-23-OXA AVERMECTIN ANALOGS ARE ACTIVE ANTHELMINTIC AGENTS

BACKGROUND OF THE INVENTION

Avermectin compounds have been known for some time as potent anthelmintic agents and substantial research has been carried out preparing various substituted variations of such compounds. Some of the avermectin compounds have become commercially available as potent broad-spectrum anthelmintic and antiparasitic agents in animal health and agriculture. See U.S. Pat. No. 4,310,519 to Albers-Schonberg et al and 4,199,569 to Chabala et al. Applicants are not aware of any avermectin compounds where the 23-ring carbon has been replaced by a heteroatom.

SUMMARY OF THE INVENTION

This invention is concerned with the preparation of 23-nor-23-oxa avermectin compounds that are prepared from avermectin natural products or derivatives thereof in a series of reactions that first opens the avermectin spiroketal ring containing the C23 ring carbon atom. The 23-carbon atom is then replaced by an oxygen containing group which may also have additional substituents thereon and the compound is then ring closed to prepare the desired compounds. The 23-nor-23-oxa compounds are highly effective anthelmintic and antiparasitic agents in animal health and agriculture.

DESCRIPTION OF THE INVENTION

The compounds of the instant invention are best realized in the following structural formula.

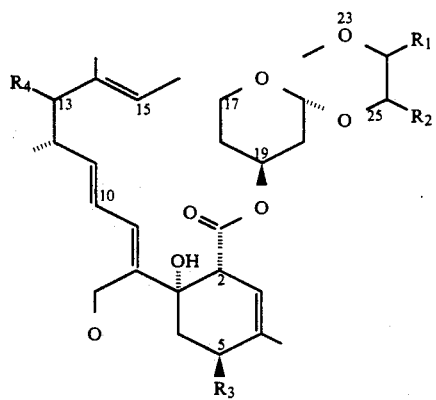

where $R_1$ and $R_2$ are independently hydrogen, $C_1-C_{10}$ alkyl, $C_2-C_{10}$ alkenyl, $C_2-C_{10}$ alkynyl, $C_1-C_{10}$ alkoxy $C_1-C_{10}$ alkyl or $C_1-C_{10}$ alkylthio $C_1-C_{10}$ alkyl group; a $C_3-C_8$ cycloalkyl or $C_5-C_8$ cycloalkenyl group, either of which may optionally be substituted by methylene or from 1 to 3 of $C_1-C_4$ alkyl groups or halo atoms; phenyl, phenoxy, $C_{1-10}$ alkyl phenyl, $C_2-C_{10}$ alkenyl phenyl, $C_2-C_{10}$ alkynyl phenyl, substituted $C_1-C_{10}$ alkyl wherein the substituents independently are 1 to 3 of $C_1-C_5$ alkyl, $C_3-C_8$ cycloalkyl or substituted $C_1-C_{10}$ alkyl wherein the substituents are independently 1 to 3 of hydroxy, halogen, cyano, $C_1-C_5$ alkyl thio, $C_1-C_5$ alkyl sulfinyl, $C_1-C_5$ alkyl sulfonyl, amino, $C_1-C_5$ mono or dialkyl amino, $C_1-C_5$ alkanoyl amino or $C_1-C_5$ alkanoylthio; or a 3 to 6 membered oxygen or sulfur containing heterocyclic ring which may be saturated or fully or partly unsaturated and which may optionally be substituted independently by 1 to 3 of $C_1-C_5$ alkyl or halogen; or $R_1$ and $R_2$ may be joined to form a $C_3-C_5$ methylene bridge;

$R_3$ is hydroxy, $C_1-C_5$-alkoxy, hydroximino or $-O-C_1-C_5$ alkyl-hydroximino;

$R_4$ is hydrogen, halogen, hydroxy, $C_1-C_5$ alkanoyloxy, $(C_1-C_5$-alkoxy$)_n$ where n is 1-4,

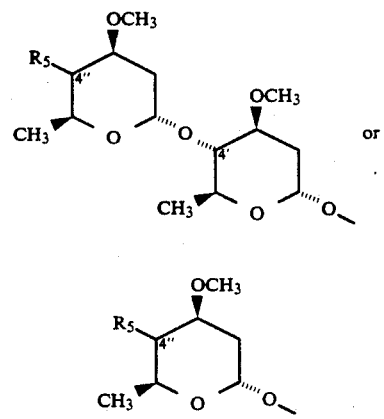

where $R_5$ is hydroxy, oxo, $(C_1-C_5$ alkyl$)_m$ amino, $C_1-C_5$ alkanoyl amino, $(C_1-C_5$ alkyl$)$ $(C_1-C_5$ alkanoyl$)$ amino, $C_1-C_5$ alkyl-S(O)$_m$, hydroxy substituted $C_1-C_5$ alkyl S(O)$_m$, where m is 0, 1 or 2 or $(C_1-C_5$-alkoxy$)_n$ where $n=1-4$.

In the foregoing structural formula and throughout the instant specification the alkyl, groups are intended to be of either a straight or branched configuration. The $(C_1-C_5$ alkoxy$)_n$ is intended to include alkoxy and polyalkoxy groups of either a straight or branched configuration and where the polyalkoxy group can independently vary as to carbon atom content and configuration.

Preferred compounds of the instant invention are realized in the foregoing structural formula wherein:

$R_1$ and $R_2$ are independently hydrogen, $C_1-C_5$ alkyl, $C_2-C_5$ alkenyl, $C_1-C_5$ alkoxy, a $C_5-C_6$ cycloalkyl or $C_5-C_6$ cycloalkenyl group, either of which may optionally be substituted by methylene or from 1 to 3 of $C_1-C_4$ alkyl groups; phenyl, phenoxy, $C_{1-5}$ alkyl phenyl, $C_2-C_5$ alkenyl phenyl, substituted $C_1-C_5$ alkyl wherein the substituents independently are 1 to 3 of $C_1-C_3$ alkyl, $C_1-C_3$ alkyl thio, $C_1-C_3$ alkyl sulfinyl, $C_1-C_3$ alkyl sulfonyl, or a 5 to 6 membered oxygen or sulfur containing heterocyclic ring which may be saturated or fully or partly unsaturated; or $R_1$ and $R_2$ may be joined to form a $C_3-C_5$ methylene bridge;

$R_3$ is hydroxy, $C_1-C_3$-alkoxy, $C_1-C_3$-alkanoyloxy hydroximino or $-O-C_1-C_5$ alkyl-hydroximino;

$R_4$ is hydrogen, halogen, hydroxy, $C_1-C_3$-alkanoyloxy, $(C_1-C_3$ alkoxy$)$, where n is 1-2,

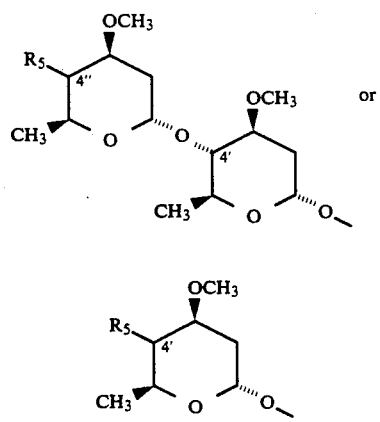

where $R_5$ is hydroxy, $C_1-C_3$ alkyl amino, $C_1-C_3$ alkanoyl amino, $(C_1-C_3$ alkyl$)(C_1-C_3$ alkanoyl$)$ amino, $C_1-C_3$ alkyl-$S(O)_m$, hydroxy substituted $C_1-C_3$ alkyl $S(O)_m$, where m is 0, 1 or 2 or $(C_1-C_3$-alkoxy$)_n$ where n=1–4.

More preferred compounds of the instant invention are realized in the foregoing structure where:

$R_1$ is hydrogen, $C_1-C_4$-alkyl;

$R_2$ is hydrogen, $C_1-C_5$ alkyl, $C_2-C_5$ alkenyl, $C_1-C_5$ alkoxy, a $C_5-C_6$ cycloalkyl or $C_5-C_6$ cycloalkenyl group, phenyl, substituted $C_1-C_5$ alkyl wherein the substituents independently are 1 to 3 of $C_1-C_3$ alkyl; or $R_1$ and $R_2$ may be joined to form a $C_3-C_4$ methylene bridge;

$R_3$ is hydroxy, hydroximino or —O—$C_1-C_2$ alkyl-hydroximino;

$R_4$ is hydrogen, halogen, hydroxy, $C_1-C_2$-alkanoyloxy, $(C_1-C_3$ alkoxy$)_n$ where n is 1–2,

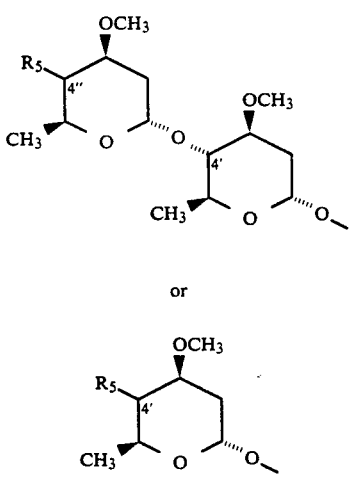

where $R_5$ is hydroxy, $C_1-C_2$ alkyl amino, $C_1-C_2$ alkanoyl amino, $(C_1-C_2$ alkyl$)(C_1-C_2$ alkanoyl$)$ amino, $C_1-C_2$ alkyl-$S(O)_m$, hydroxy substituted $C_1-C_2$ alkyl $S(O)_m$, where m is 0, 1 or 2.

Examples of preferred compounds of this invention are:

23-nor-23-oxa-24-desmethyl-25-desbutyl-24-phenyl ivermectin B1;
23-nor-23-oxa-24-desmethyl-25-desbutyl-25-phenyl ivermectin B1;
23-nor-23-oxa-24-desmethyl-25-desbutyl-24-(4-methyl)-phenyl ivermectin B1;
23-nor-23-oxa-24-desmethyl-25-desbutyl-25-(4-methyl)-phenyl ivermectin B1;
23-nor-23-oxa-24-desmethyl-25-desbutyl-24-methyl ivermectin B1;
23-nor-23-oxa-24-desmethyl-25-desbutyl-25-methyl ivermectin B1;
23-nor-23-oxa-24-desmethyl-25-desbutyl-24-t-butyl ivermectin B1;
23-nor-23-oxa-24-desmethyl-25-desbutyl-25-t-butyl ivermectin B1;
23-nor-23-oxa-24-desmethyl-25-desbutyl-24-cyclohexyl ivermectin B1;
23-nor-23-oxa-24-desmethyl-25-desbutyl-25-cyclohexyl ivermectin B1;
23-nor-23-oxa-24-methyl-25-desbutyl-25-methyl ivermectin B1;
23-nor-23-oxa-24-desmethyl-25-desbutyl-24,25-cyclohexyl ivermectin B1;
23-nor-23-oxa-24-desmethyl-ivermectin B1;
23-nor-23-oxa-24-desmethyl-25-desbutyl-25-(2-butyl) ivermectin B1;
23-nor-23-oxa-24-desmethyl-25-desbutyl-25-isopropyl-ivermectin B1;
23-nor-23-oxa-24-desmethyl-25-desbutyl-25-ethyl-ivermectin B1;
23-nor-23-oxa-24-desmethyl-25-desbutyl-25-[2-(4-methylpent-2-enyl)]ivermectin B1;
23-nor-23-oxa-24-desmethyl-5-ketoxime-ivermectin B1;
23-nor-23-oxa-24-desmethyl-4''-epi-amino-4''deoxy-ivermectin B1;
23-nor-23-oxa-24-desmethyl-25-desbutyl-4''-epi-acetyl(-methyl)amino-4''-deoxy-ivermectin B1;
23-nor-23-oxa-24-desmethyl-25-desbutyl-25-cyclohexyl ivermectin B1 aglycone;
23-nor-23-oxa-24-methyl-25-desbutyl-25-methyl ivermectin B1 aglycone;
23-nor-23-oxa-24-desmethyl-25-desbutyl-25-methyl-13-O-methoxymethyl-ivermectin B1 aglycone.
23-nor-23-oxa-24-desmethyl-25-desbutyl-25-phenyl-13-deoxy-13-chloro-ivermectin B1 aglycone;
23-nor-23-oxa-24-desmethyl-25-desbutyl-25-phenyl-13-deoxy-13-fluoro-ivermectin B1 aglycone;
23-nor-23-oxa-24-methyl-25-desbutyl-25-isopropyl-4''-deoxy-4''-(2-acetylaminoethyl)thio-ivermectin B1;
23-nor-23-oxa-24-desmethyl-25-desbutyl-25-isopropyl-4''-deoxy-4''-(2-acetylaminoethyl)sulfonyl-ivermectin B1.

The compounds of the instant invention are prepared in a series of reactions beginning with the natural product avermectins or derivatives thereof. The reaction sequence used to prepare the instant compounds is shown in Reaction Scheme 1. For clarity and simplicity, the Reaction Scheme shows only carbon atoms numbered 17 and higher.

REACTION SCHEME I

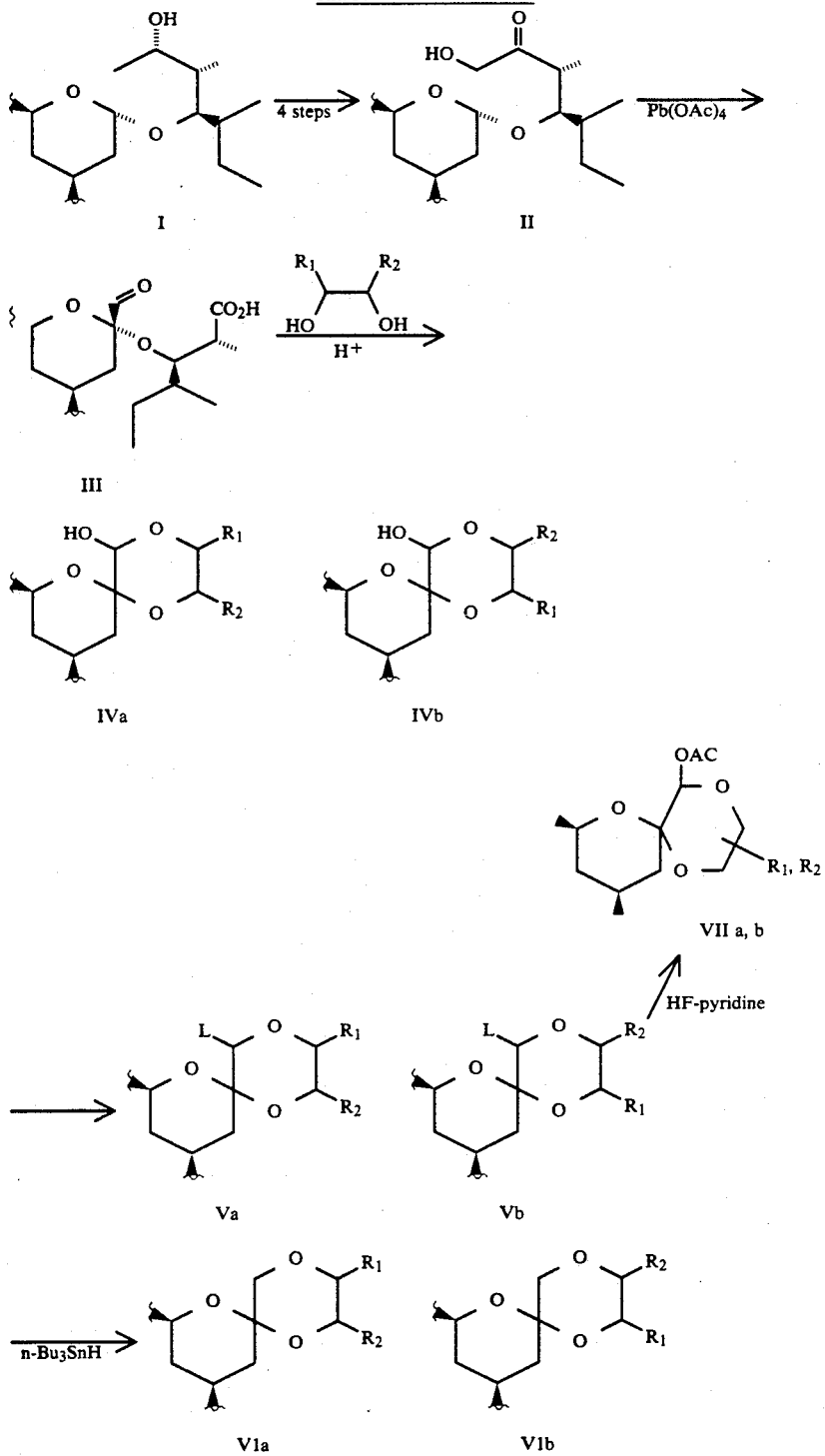

The critical intermediate III is prepared in six steps from avermectin starting material I (for purposes of example shown as avermectin B2a) with the 6,6-spiroketal ring system and the appropriate substituents at the remainder of the molecule or with a substitution pattern from which the substituent groups at the remainder of the molecule can be prepared after the synthesis of the instant compounds.

Compound I, suitably protected at the hydroxy groups, is reacted with an oxidizing agent such as oxalyl chloride in DMSO in the presence of at least 2 equivalents of a base to react with the HCl liberated during the course of the reaction. The reaction is carried out initially in the cold at temperatures less than 0° C. and preferably less than −50° C. and is generally complete in from 1 to 10 hours affording the 23-keto compound.

In the next step the 23-keto compound is reacted with an alkali metal bis(trimethylsilyl)amide to form the enol ether with a 22,23-double bond. The reaction is carried out in the cold at a temperature less than 0° C. and preferably less than −50° C. under an inert atmosphere in a non-reactive solvent such as a hydrocarbon, preferably an alkane or other nonpolar solvents such as tetrahydrofuran that will remain liquid at reaction temperatures. Generally mixtures of $C_6$ to $C_9$ alkanes, preferably hexanes, are used. The reaction is generally complete in from 1 to 10 hours. The choice of the base in this reaction is very important since it is well known that strong bases readily epimerize the 2-position of the avermectin molecule and rearrange the 3,4-double bond to give analogs of low biological potency. It was found that from a selection of numerous bases, an alkali metal bis(-trimethylsilyl)amide is capable of forming the desired silyl enol ether without any further side reactions.

In the next step the 22,23-double bond is epoxidized with a mild oxidizing agent, preferably a peroxy acid such as meta-chloroperbenzoic acid. The reaction is carried out in an inert solvent such as a chlorinated hydrocarbon such as chloroform or methylene chloride and the like at a temperature of from 0° to 50° C. and is generally complete in about 10 minutes to 2 hours.

In the final step of the reaction of compound I to prepare compound II the 22,23-epoxide is treated with acidic methanol to hydrolize the epoxide and form compound II. The reaction is carried out at about room temperature and is generally complete in from 5 minutes to 2 hours.

In the foregoing series of reactions the intermediates may be isolated and purified, however it has not been found necessary to do so and if desired, the reactions may be carried out in a single reaction vessel, only isolating compound II at the conclusion of the series of four reaction steps.

Compound II is then cleaved to form the critical intermediate III. Compound II is treated with lead tetraacetate which cleaves the 22,23-bond affording critical intermediate III.

Compound III is transketallized to produce cyclized products IVa/b in a single step with 1,2-diols in chlorinated solvents such as methylene chloride or chloroform at 0° C. to room temperature with acid catalysis to yield isomeric mixtures of IVa and IVb. Mono- or di-substituted diols may be used in this reaction. Racemic or enantiamerically pure diols may be used in this reaction. Organic acids, such as para-toluensulfonic acid or benzenesulfonic acid, are preferred. These transketallization reactions are rapid and are generally complete within 5 min. to 2 hours. different method of effecting reduction is employed. Treatment of the acetate or trifluoroacetate with catalytic boron trifluoride etherate (10 mole percent) in methylene chloride with excess triethyl silane yielded VIa/b. These reactions were best performed at −78° C. and then gradually warmed to 0° C. and were complete within minutes to one hour.

Treatment of compounds VIa/b or VIIa/b with 1% sulfuric acid in methanol at room temperature for twelve hours allows for the preparation of the aglycones in deprotected form. If this reaction is run for four hours in isopropanol using 1% sulfuric acid, formation of the monosaccharides occurs.

Deprotection is best achieved using HF.pyridine in THF at room temperature for 12-48 hours. Deprotection of Va/b to yield VIIa/b under the identical conditions also proceeds readily.

Separation of isomers, if present, is possible while at the IVa/b, Va/b, VIa/v and deprotected stages. The isomers may be separated, if desired, by thin layer preparative chromatography, flash chromatography or high pressure liquid chromatography (normal or reverse phase). Isomer separation at these various stages is dictated primarily by ease of separation at any given point.

The foregoing series of reactions is carried out using protecting groups on the reactive functions, such as hydroxy groups, on the avermectin molecule. Following the completion of the reaction sequence, the protecting groups may be removed to afford the unprotected final product. However, the final product contains several asymmetric centers which would result in a possibility of many stereoisomers The resultant C22-anomeric alcohol formed (the C22-hydroxyl of IVa and IVb) may be further functionalized by converting it into a leaving group, represented by the "L" shown in structures Va and Vb. Representative leaving groups include, but are not restricted to, chlorides, bromides, phenyl selenides, phenyl sulfides, acetates, trifluoroacetates, or pentafluorothionoformates. The latter three functional groups are readily introduced by O-acylation reactions. The O-acylation is best performed using chlorinated solvents such as methylene chloride or chloroform at 0° C. to room temperature in the presence of a base, preferably triethylamine, diisopropylethylamine, pyridine or 4-dimethylaminopyridine. The former four groups (Cl, Br, PhS and PhSe) are readily introduced using triphenylphosphine under Mitsunobu-like conditions (eg. $Ph_3PCl_2$, $Ph_3PBr_2$, $Ph_3P/CBr_4$, $PH_3P/PhSSPh$, $Ph_3P/PhSeSePh$, $PH_3P/N$-Phenylselenophthalimide) in inert solvents such as methylene chloride, chloroform, benzene or toluene.

The leaving group "L" in Va/b may be replaced with hydrogen under reductive conditions. Where "L" represents Cl, Br, PhS, PhSe or OC(S)OPh(Fs), the reduction is most readily effected by heating Va/b to 50°-150° C. in the presence of excess tri-n-butyl tin hydride and a radical iniator such as benzoyl peroxide or azobis (2-propionitrile). These reductions may be performed in neat tri-n-butyl tin hydride or using benzene or toluene as a co-solvent for the reaction. The reductions generally are complete in five minutes to one hour. Where "L" in Va/b represents $OC(O)CH_3$ or $OC(O)CF_3$, a for each product. The isomers can be readily separated from each other prior to the removal of the protecting groups using chromatographic techniques, such as column chromatography. If the protecting groups are removed, the separation of the isomer is still readily accomplished chromatographically using thin layer or preparative layer chromatography or reverse phase high pressure liquid chromatography. The mixtures of stereoisomers as well as the isolated stereoisomers have been found to have substantial activity as antiparasitic or insecticidal products.

Some additional substituents can be prepared on the instant compound using techniques known to those skilled in the art, such as the introduction of alkylthio or substituted alkylthio substituents at the 4'-and 4"-positions and the oxidized derivatives thereof. The substituents can be synthesized either prior to the preparation of the 23-nor-23-oxa ring system or after the 23-nor-23-oxa ring system is prepared. However, to avoid undesired side-reactions, in particular where the alkylthio group contains reactive substituents, it is often preferred to prepare the 4'- or 4"-alkylthio substituent after the reactions for the preparation of the 23-nor-23-oxa ring system have been completed.

The preparation of the 4'- and 4"-alkylthio compounds of this invention is best accomplished when the avermectin starting materials are protected at the 5-hydroxy position to avoid substitution at this position. With this position protected, the reactions may be carried out at the 4"- or 4'-positions without affecting the remainder of the molecule. The 5-hydroxy group is protected by a tert.-butyldimethylsilyl group before displacement at the 4"- or 4'-hydroxyl group has occurred. The 7-hydroxy group is very unreactive and need not be protected.

The preparation of the 4'- and 4"-alkylthio compounds requires that the avermectin starting materials are converted into derivatives with good leaving groups at the 4"- or 4'-position, preferably halo- or alkyl-substituted sulfonyl groups, more preferably trifluoromethanesulfonyl- or iodo-groups. Subsequently, these leaving groups are displaced by sulfur-containing nucleophiles to obtain the desired 4"-deoxy-4"-alkylthio avermectin derivatives (which also may be modified further).

The 4"- or 4'-alkyl substituted sulfonyl intermediate is prepared from the 5-position protected avermectin using the appropriate sulfonic anhydride or the appropriate sulfonyl chloride in an inert solvent such as a chlorinated hydrocarbon, tetrahydrofuran (THF), or ether, preferably methylene chloride, in the presence of base at $-15°$ to $10°$ C. over a period of 15 minutes to 1 hour. The 4"- or 4'-alkyl substituted sulfonyl compound may be isolated using techniques known to those skilled in the art. Then the 4"- or 4'-sulfonylavermectin is substituted at the 4"- or 4'-position by sulfur-containing nucleophiles. The reaction is carried out at or near at room temperature in an inert solvent such as dimethylformamide (DMF), dimethylsulfoxide (DMSO), THF, chlorinated hydrocarbons, or ether, preferably DMF, with the desired thiol nucleophile, either the metallic thiol or a thiol with a base such as potassium carbonate at $0°$ to $25°$ C. over a period of 1 to 4 hours. It has been found useful to include in the reaction mixture a small quantity of crown ethers such as 18-crown-6 (1,4,7,10,13,16-hexaoxacyclooctadecane). The presence of the crown ether facilitates the reaction and generally significantly reduces the duration of the reaction. The products are isolated using known techniques.

There are two possible epimers at the 4"- or 4'-position; one with the stereochemistry exactly as in the natural avermectins with an equatorial (or $\alpha$) substituent and one with the axial (or $\beta$) configuration. The latter is called 4"- or 4'-epi. The reaction with strong nucleophiles results predominantly in the product with the inverted configuration. The reaction with hard nucleophiles usually gives both compounds, which are separable, but since both possess high biological activities, they need not be separated. Both epimers are considered part of this invention, either separate or in a mixture.

Nucleophilic substitution of the leaving group can be also accomplished by iodine, by adding a halogen salt to a stirred solution of the avermectin substituted with a good leaving group at the 4"-position in DMF, DMSO, THF or a chlorinated hydrocarbon and allowing the reaction to stir at room temperature form 1 to 6 hours. The product is isolated using known techniques. The 4"-halogen atom can, in turn, be displaced by other nucleophiles, including other sulfur-containing nucleophiles.

In addition, the sulfur-containing 4"-substituent can be further modified. Oxidation of the 4"-sulfur in an unreactive solvent with an oxidizing agent such as m-chloroperbenzoic acid at $-15°$ to $25°$ C. for a period of 30 minutes to 2 hours gives the sulfoxide and the sulfone. Both enantiomers of the sulfoxide are obtained.

The sulfur-containing 4'-and 4"-groups can be oxidized to the corresponding sulfinyl and sulfonyl groups in a solvent such as a chlorinated hydrocarbon, THF, ether, or lower alcohol, preferably methylene chloride. An oxidizing agent such as a peracid, preferably m-chloroperbenzoic acid, is added to a solution of the 4"- or 4'-substituted avermectin. By varying the temperature (from $-30°$ C. to room temperature) and the number of equivalents of oxidizing agent, the relative yields of the sulfoxide and sulfone can be controlled. The products are separated and isolated using techniques known to those skilled in the art.

Further modifications of the side chain can be accomplished when a thio-alcohol is used as the nucleophile. The hydroxyl group of the alcohol on the sulfur-containing side chain can undergo any of the reactions and chemistry that is possible at the 4"- or 4'-hydroxy group, including, but not limited to, those described herein.

Following the desired substitution and modification at the 4"-position, the 5-hydroxy group is deprotected and, if desired, modifications of the molecule at the 5-position can occur.

The foregoing reactions carried out at the 4"-position of the avermectin can be carried out at the 4'-position of the avermectin monosacchoride to affect the correspondingly substituted monosacchoride derivatives.

The preparation of additional derivatives of the various reactive substituents can also be carried out using procedures well known to those skilled in the art. See for example U.S. Pat. No. 4,906,619 to Eskola et al, for the preparation of various alkylated avermectins; U.S. Pat. No. 4,427,663 to Mrozik for the preparation of various 4'- or 4"-keto or amino derivatives; U.S. Pat. No. 4,201,861 to Mrozik et al, for the preparation of various, acylated avermectins; U.S. Pat. Nos. Re 32,006 and RE 32,034 to Chabala et al for the preparation of various 13-substituted and 13-unsubstituted avermectins; U.S. Pat. No. 4,200,981 to Fisher et al for the preparation of various 5-alkylated compounds; and U.S. Pat. No. 4,895,837 to Mrozik for a discussion of various procedures for the protection of avermectin compounds.

The instant compounds are potent endo- and ecto-antiparasitic agents against parasites particularly helminths, ectoparasites, insects, and acarides, infecting man, animals and plants, thus having utility in human and animal health, agriculture and pest control in household and commercial areas.

The disease or group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats, fish, buffalo, camels, llamas, reindeer, laboratory animals, furbearing animals, zoo animals and exotic species and poultry. Among the helminths, the group of worms described as nematodes causes widespread and often times serious infection in various species of animals. The most common genera of nematodes infecting the animals referred to above are Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Habronema, Druschia, Heterakis, Toxocara, Ascaridia, Oxyuris, Anchlostoma, Uncinaria, Toxascaris and Parascaris. Certain of these, such as Nematodirus, Cooperia, and Oesophagostomum attack primarily the intestinal tract while others, such as Haemonchus and Ostertagia, are more prevalent in the stomach while still others such as Dictyocaulus are found in the lungs. Still other parasites may be located in other tissues and organs of the body such as the heart and blood vessels, subcutaneous and lymphatic tissue and the like. The parasitic infections known as helminthiases lead to anemia, malnutrition, weakness, weight loss, severe damage to the walls of the intestinal tract and other tissues and organs and, if left untreated, may result in death of the infected host. The compounds of this invention have unexpectedly high activity against these parasites, and in addition are also active against Dirofilaria in dogs and cats, Nematospiroides, Syphacia, Aspiculuris in rodents, arthropod ectoparasites of animals and birds such as ticks, mites, lice, fleas, blowflies, in sheep Lucilia sp., biting insects and such migrating diperous larvae as Hypoderma sp. in cattle, Gastrophilus in horses, and Cuterebra sp. in rodents and nuisance flies including blood feeding flies and filth flies.

The instant compounds are also useful against parasites which infect humans. The most common genera of parasites of the gastro-intestinal tract of man are Ancylostoma, Necator, Ascaris, Strongyloides, Trichinella, Capillaria, Trichuris, and Enterobius. Other medically important genera of parasites which are found in the blood or other tissues and organs outside the gastrointestinal tract are the filiarial worms such as Wuchereria, Brugia, Onchocerca and Loa, Dracunuculus and extra intestinal stages of the intestinal worms Strongyloides and Trichinella. The compounds are also of value against arthropods parasitizing man, biting insects and other dipterous pests causing annoyance to man.

The compounds are also active against household pests such as the cockroach, Blatella sp., clothes moth, Tineola sp., carpet beetle, Attagenus sp., the housefly Musca domestica as well as fleas, house dust mites, termites and ants.

The compounds are also useful against insect pests of stored grains such as Tribolium sp., Tenebrio sp. and of agricultural plants such as aphids, (Acyrthiosiphon sp.); against migratory orthopterans such as locusts and immature stages of insects living on plant tissue. The compounds are useful as a nematocide for the control of soil nematodes and plant parasites such as Meloidogyne sp. which may be of importance in agriculture. The compounds are also highly useful in treating acerage infested with fire ant nests. The compounds are scattered above the infested area in low levels in bait formulations which are brought back to the nest. In addition to a direct-but-slow onset toxic effect on the fire ants, the compound has a long-term effect on the nest by sterilizing the queen which effectively destroys the nest.

The compounds of this invention may be administered in formulations wherein the active compound is intimately admixed with one or more inert ingredients and optionally including one or more additional active ingredients. The compounds may be used in any composition known to those skilled in the art for administration to humans and animals, for application to plants and for premise and area application to control household pests in either a residential or commercial setting. For application to humans and animals to control internal and external parasites, oral formulations, in solid or liquid or parenteral liquid, implant or depot injection forms may be used. For topical application dip, spray, powder, dust, pour-on, spot-on, jetting fluid, shampoos, collar, tag or harness, may be used. For agricultural premise or area application, liquid spray, powders, dust, or bait forms may be used. In addition "feed-through" forms may be used to control nuisance flies that feed or breed in animal waste. The compounds are formulated, such as by encapsulation, to lease a residue of active agent in the animal waste which controls filth flies or other arthropod pests.

These compounds may be administered orally in a unit dosage form such as a capsule, bolus or tablet, or as a liquid drench where used as an anthelmintic in mammals. The drench is normally a solution, suspension or dispersion of the active ingredient usually in water together with a suspending agent such as bentonite and a wetting agent or like excipient. Generally, the drenches also contain an antifoaming agent. Drench formulations generally contain from about 0.001 to 0.5% by weight of the active compound. Preferred drench formulations may contain from 0.01 to 0.1% by weight. The capsules and boluses comprise the active ingredient admixed with a carrier vehicle such as starch, talc, magnesium stearate, or di-calcium phosphate.

Where it is desired to administer the instant compounds in a dry, solid unit dosage form, capsules, boluses or tablets containing the desired amount of active compound usually are employed. These dosage forms are prepared by intimately and uniformly mixing the active ingredient with suitable finely divided diluents, fillers, disintegrating agents, and/or binders such as starch, lactose, talc, magnesium stearate, vegetable gums and the like. Such unit dosage formulations may be varied widely with respect to their total weight and content of the antiparasitic agent depending upon factors such as the type of host animal to be treated, the severity and type of infection and the weight of the host.

When the active compound is to be administered via an animal feedstuff, it is intimately dispersed in the feed or used as a top dressing or in the form of pellets or liquid which may then be added to the finished feed or optionally fed separately. Alternatively, feed based individual dosage forms may be used such as a chewable treat. Alternatively, the antiparasitic compounds of this invention may be administered to animals parenterally, for example, by intraruminal, intramuscular, intravascular, intratracheal, or subcutaneous injection in which the active ingredient is dissolved or dispersed in a liquid carrier vehicle. For parenteral administration, the active material is suitably admixed with an acceptable vehicle, preferably of the vegetable oil variety such as peanut oil, cotton seed oil and the like. Other parenteral vehicles such as organic preparation using solketal, glycerol formal, propylene glycol, and aqueous parenteral formulations are also used. The active compound or compounds are dissolved or suspended in the parenteral formulation for administration; such formulations generally contain from 0.0005 to 5% by weight of the active compound.

Although the antiparasitic agents of this invention find their primary use in the treatment and/or prevention of helminthiasis, they are also useful in the prevention and treatment of diseases caused by other parasites, for example, arthropod parasites such as ticks, lice, fleas, mites and other biting arthropods in domesticated animals and poultry. They are also effective in treatment of parasitic diseases that occur in other animals including humans. The optimum amount to be employed for best results will, of course, depend upon the particular compound employed, the species of animal to be treated and the type and severity of parasitic infection or infestation. Generally good results are obtained with our novel compounds by the oral administration of from about 0.001 to 10 mg per kg of animal body weight, such total dose being given at one time or in divided doses over a relatively short period of time such as 1–5 days. With the preferred compounds of the invention, excellent control of such parasites is obtained in animals by administering from about 0.025 to 0.5 mg per kg of body weight in a single dose. Repeat treatments are given as required to combat re-infections and are dependent upon the species of parasite and the husbandry techniques being employed. The techniques for administering these materials to animals are known to those skilled in the veterinary field.

When the compounds described herein are administered as a component of the feed of the animals, or dissolved or suspended in the drinking water, compositions are provided in which the active compound or compounds are intimately dispersed in an inert carrier or diluent. By inert carrier is meant one that will not react with the antiparasitic agent and one that may be administered safely to animals. Preferably, a carrier for feed administration is one that is, or may be, an ingredient of the animal ration.

Suitable compositions include feed premixes or supplements in which the active ingredient is present in relatively large amounts and which are suitable for direct feeding to the animal or for addition to the feed either directly or after an intermediate dilution or blending step. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like. The active compounds are intimately dispersed throughout the carrier by methods such as grinding, stirring, milling or tumbling. Compositions containing from about 0.005 to 2.0% weight of the active compound are particularly suitable as feed premixes. Feed supplements, which are fed directly to the animal, contain from about 0.0002 to 0.3% by weight of the active compounds.

Such supplements are added to the animal feed in an amount to give the finished feed the concentration of active compound desired for the treatment and control of parasitic diseases. Although the desired concentration of active compound will vary depending upon the factors previously mentioned as well as upon the particular compound employed, the compounds of this invention are usually fed at concentrations of between 0.00001 to 0.002% in the feed in order to achieve the desired antiparasitic result.

In using the compounds of this invention, the individual compounds may be prepared and used in that form. Alternatively, mixtures of the individual compounds may be used, or other active compounds not related to the compounds of this invention.

The compounds of this invention are also useful in combatting agricultural pests that inflict damage upon crops while they are growing or while in storage. The compounds are applied using known techniques as sprays, dusts, emulsions and the like, to the growing or stored crops to effect protection from such agricultural pests.

The following examples are provided in order that this invention might be more fully understood; they are not to be construed as limitative of the invention.

EXAMPLE 1

4″,5-Di-O-t-Butyldimethylsilyl-avermectin B2a

To a solution of 58.2 g (65 mmol) of dried avermectin B2a in 400 mL of sieve-dried dimethylformamide and 30 mL of freshly distilled triethylamine was added a solution of 29.8 g (198 mmol, 3 equiv.) of t-butyldimethylsilyl chloride in 200 mL of dichloromethane. The mixture was stirred at room temperature 16 hours then poured into ice water and extracted with dichloromethane. The organic phases were combined and washed with water, brine, and dried over magnesium sulfate. Evaporation of the solvent afforded an oil which was purified by silica gel liquid chromatography using 20% ethyl acetate-hexanes to yield 34.2 g of 4″,5-di-O-t-butyldimethylsilyl-avermectin B2a characterized by its NMR and mass spectra.

EXAMPLE 2

4″,5-Di-O-t-Butyldimethylsilyl-23-oxo-avermectin B2a

A 5-L 3-neck flask equipped with a thermometer, mechanical stirrer, and dropping funnel was charged with 400 mL of dichloromethane and 16 mL (0.185 mol) of oxalyl chloride. The solution was cooled to $-70°$ C., under nitrogen while a solution of 25 mL (0.350 mol) of dimethylsulfoxide in 200 mL of dichloromethane was added dropwise over 30 minutes keeping the internal temperature below $-65°$ C. The mixture was stirred at $-70°$ C. for 1 hour. A solution of 114.75 g (0.103 mmol) of 4″,5-di-O-t-butyldimethyl-silyl-avermectin B2a in 900 mL of dichloromethane was then added dropwise over 45 minutes keeping the temperature of the mixture below $-65°$ C. After an additional 2 hours at $-70°$ C., 115 mL of triethylamine was added dropwise over 10 minutes again keeping the temperature below $-65°$ C. The reaction was then stirred at approximately $10°$ C. for 1 hour before the solvent was removed in vacuo. The residue was taken up in 1.5 L of ether and washed with 500 mL of water. The aqueous layer was extracted with 500 mL of ether. The combined ether layers were washed sequentially with $2 \times 1$ L of water, 1 L of saturated sodium bicarbonate, and 1 L of brine, then dried over magnesium sulfate. The solvent was removed to afford 100 g of yellow foam purified by column chromatography (4 kg silica gel, eluted with 5–25% ethyl acetate-hexane eluant). The product was obtained as a yellow foam (101 g, 88% yield). NMR (300 MHz, TMS) δ0.08 (d, J=6 Hz), 0.14 (s), 0.9 (s), 0.93 (s), 0.98 (m), 1.16 (d, J=7 Hz), 1.2 (d, J=Hz), 1.24 (d, J=7 Hz), 1.45 (s), 1.5 (m), 1.8 (s), 2.22 (m), 2.44 (m), 3.12 (t, J=9 Hz), 3.2 (t, J=9 Hz), 3.32 (s), 3.42 (s), 3.6 (m), 3.81 (d, J=6 Hz), 3.93 (s), 3.98 (sh s), 4.44 (d, J=6 Hz), 4.62 (dq, J=2,14 Hz), 4.74 (d, J=3 Hz), 4.93 (t, J=7 Hz), 5.3 (m), 5.7 (m), 5.8 (m); mass spec: FAB 1123 (M+Li).

EXAMPLE 3

4″,5-Di-O-t-Butyldimethylsilyl-7-O-trimethylsilyl-23-O-trimethylsilyloxy-avermectin B1a To a solution of 101 mg (0.09 mmol) of 4″,5-di-O-t-butyldimethylsilyl-23-oxo-avermectin B2a in 2 mL of distilled tetrahydrofuran at −78° C. was added 0.400 mL of a 1.0M solution of lithium bis(trimethylsilyl)amide in a mixture of hexanes. The mixture was stirred at −78° C., under argon, for 1 hour before 0.20 mL of the supernatant of a centrifuged 1:3 mixture of triethylamine and trimethylchlorosilane was added dropwise via a syringe. After another 30 minutes, 2 ml of a saturated aqueous sodium bicarbonate solution was added and the mixture was allowed to warm to room temperature. The reaction mixture was then partitioned between water and ether and the ethereal extracts were combined and dried over magnesium sulfate. Filtration and evaporation of the ther afforded 120 mg of 4″,5-di-O-t-butyldimethylsilyl-7-O-trimethylsilyl-23-O-trimethylsilyloxy-avermectin B1a characterized by its NMR $\delta$0.08 (d, J=6 Hz), 0.12 (s), 0.18 (s), 0.88 (s), 0.92 (s), 1.18 (d, J=8 Hz), 1.23 (d, J=8 Hz), 1.26 (d, J=8 Hz), 1.5 (s), 1.51 (m), 1.78 (s), 2.3 (m), 2.58 (m), 3.12 (t, J=9 Hz), 3.22 (t, J=9 Hz), 3.25 (s), 3.32 (s), 3.4 (s), 3.8 (d, J=6 Hz), 3.82 (m), 3.98 (s), 4.39 (d, J=4 Hz), 4.6 (q, J=16 Hz), 4.68 (sh d, J=2 Hz, C22H), 4.8 (d, J=3 Hz), 4.9 (m), 5.1 (m), 5.25 (d, J=3 Hz), 5.45 (s), 5.7 (m).

EXAMPLE 4

4″,5-Di-O-t-Butyldimethylsilyl-7-O-trimethylsilyl-22-hydroxy-23-oxo-avermectin B2a To a solution of 135 mg (0.107 mmol) of 4″,5-Di-O-t-butyldimethylsilyl-7-O-trimethylsilyl-23-O-trimethylsilyloxy-avermectin B1a in 2 mL of dichloromethane was added a solution of 21 mg (0.12 mmol) of m-chloroperbenzoic acid in 1 mL of dichloromethane in one portion. After 20 minutes at 20° C., 0.2 mL of dimethylsulfide was added. The mixture was stirred another 30 minutes before the addition of aqueous sodium bicarbonate and extraction with ethyl acetate. The combined organic fractions were dried, filtered, and evaporated to afford 150 mg of solid. This product mixture was separated by preparative thin layer chromatography (20% ethyl actate-hexane) to afford 40 mg of 4″,5-Di-O-t-butyldimethylsilyl-7-O-trimethylsilyl-22-hydroxy-23-oxo-avermectin B2a. NMR $\delta$0.08 (d, J=6 Hz), 0.14 (s), 0.88 (s), 0.92 (s), 0.96 (d, J=6 Hz), 0.98 (d, J=6 Hz), 1.16 (d, J=7 Hz), 1.20 (d, J=6 Hz), 1.23 (d, J=6 Hz), 1.43 (s), 1.50 (s), 1.52 (m), 1.78 (s), 2.24 (m), 2.4 (dd, J=6,12 Hz), 2.58 (m), 3.12 (t, J=9 Hz), 3.22 (t, J=9 Hz), 3.3 (s), 3.32 (s), 3.4 (s), 3.62 (m), 3.82 (m), 3.82 (d, J=6 Hz), 3.92 (d, J=7 Hz), 3.97 (s), 4.38 (d, J=3 Hz), 4.6 (q, J=15 Hz), 4.77 (d, J=3 Hz), 4.83 (m), 5.05 (br d, J=7 Hz), 5.25 (d, J=3 Hz), 5.5 (s), 5.7 (m); mass spec. FAB 1212 (M+Li+H).

EXAMPLE 5

Preparation of Aldehyde-Acid

To a solution of 600 mg (0.5 mmol) of 4″,5-Di-O-t-butyldimethylsilyl-7-O-trimethysilyl-22-hydroxy-23-oxo-avermectin B2a in 6 mL of benzene in an aluminum foil-covered glass vial was added 400 mg (0.9 mmol) of lead tetraacetate in one portion. After 30 minutes at 20° C., the solution was poured into a separatory funnel containing 12 mL of water and 600 mg of sodium sulfite. The mixture was then shaken and extracted with ethyl acetate. The combined extracts were dried (MgSO$_4$), filtered, and evaporated to afford 600 mg of solid. Flash chromatography through a column of silica gel eluting with 2:1 hexane: ethyl acetate, then acetone afforded 250 mg of starting material and 230 mg of aldehyde-acid. NMR $\delta$0.08 (d, J=6 Hz), 0.13 (s), 0.89 (s), 0.92 (s), 1.15 (d, J=6 Hz), 1.18 (d, J=6 Hz), 1.20 (d, J=6 Hz), 1.26 (d, J=6 Hz), 1.5 (s), 1.53 (m), 1.78 (s), 2.3 (m), 2.78 (br s), 3.13 (t, J=9 Hz), 3.23 (t, J=9 Hz), 3.23 (s), 3.32 (s), 3.36 (m), 3.42 (br s), 3.68 (m), 3.81 (m), 3.82 (d, J=6 Hz), 3.98 (s), 4.38 (s), 4.6 (q, J=15 Hz), 4.79 (d, J=2 Hz), 4.86 (br s), 5.12 (br s), 5.3 (s), 5.44 (s), 5.7 (m).

EXAMPLE 6

Preparation of 4″,5-bis-O-tert-butyldimethylsily-7-O-trimethylsilyl-23-nor-23-oxa-24-desmethyl-25-des-2-butyl-22-hydroxy-ivermectin (IVa.1)

900 mg Aldehyde-acid III (737 $\mu$mol) was dissolved in 5 mL methylene chloride at room temperature to which was added 1 mL ethylene glycol (18 mmol) and 125 mg p-toluenesulfonic acid (726 $\mu$mol). After 15 min, the reaction was poured into 5 mL saturated NaHCO$_3$ (diluted to 50 mL with water). The solution was extracted with methylene chloride, the organic layer dried (MgSO$_4$), the solution filtered and concentrated under reduced pressure. Pure IVa.1 was obtained (497 mg, 67%) after flash chromatography on silica gel using 6:4 hexanes: ethyl acetate.

EXAMPLE 7

Preparation of 4″,5-bis-O-tert-butyldimethylsilyl-7-O-trimethylsilyl-23-nor-23-oxa-24-methyl-25-des-2-butyl-22-hydroxy-ivermectin (IVa.2) and 4″,5-bis-O-tertbutyldimethylsilyl-7-O-trimethylsilyl-23-nor-23-oxa-24-desmethyl-25-des-2-butyl-25-methyl-22-hydroxy-ivermectin (IVb.2)

500 mg Aldehyde-acid III (409 $\mu$mol) was dissolved in 3 mL methylene chloride. To this was added 1 mL 1,2-propanediol and 200 mg p-toluene-sulfonic acid. After 15 min, the solution was poured into 50 mL saturated NaHCO$_3$, extracted with methylene chloride and dried (MgSO$_4$). The solution was filtered and concentrated under reduced pressure. Flash chromatography on silica gel using 1:1 hexanes: ethyl/acetate as eluant yielded 399 mg (86%) pure IVa.2 and IVb.2 as a 1:1 mixture of isomers.

EXAMPLE 8

Preparation of 4″,5-bis-O-tert-butyldimethylsilyl-7-O-trimethylsilyl-23-nor-23-oxa-24-(R)-phenyl-25-des-2-butyl-ivermectin (IVa.3) and 4″,5-bis-O-tert-butyldimethylsilyl-7-O-trimethylsilyl-23-nor-23-oxa-24-desmethyl-25-des-2-butyl-25-(R)-phenylivermectin (IVb.3)

500 mg Aldehyde-acid III (410 $\mu$mol) was placed in 2 mL methylene chloride at room temperature to which was added 300 mg (R)-(−)-1-phenyl-1,2-ethanediol (2.17 mmol) followed by 100 mg p-toluenesulfonic acid (581 $\mu$mol). After 15 min, the reaction was poured into 10 mL saturated NaHCO$_3$, extracted with methylene chloride and dried (MgSO$_4$). The solution was filtered, the product concentrated under reduced pressure and pure IVa.3 and IVb.3 (314 mg, 64%) were obtained as a 1:1 mixture after flash chromatography on silica gel using 3:1 hexanes: ethyl acetate as eluant.

EXAMPLE 9

(Racemic) Preparation of 4″,5-bis-O-tert-butyldimethylsilyl-7-O-trimethylsilyl-23-nor-23-oxa-24-methyl-25-des-2-butyl-25-methyl-22-hydroxy-ivermectin (IVa.4)

500 mg Aldehyde-acid III (410 μmol) was placed in 2 mL methylene chloride at room temperature to which was added 0.5 mL D,L-trans-2,3-butanediol and 100 mg p-toluenesulfonic acid (581 μmol). After 15 min, the solution was poured into 20 mL saturated NaHCO$_3$, extracted with methylene chloride and dried (MgSO$_4$). The solution was then filtered, concentrated under reduced pressure and purified by flash chromatography on silica gel to yield 337 mg IVa.4 (71%).

EXAMPLE 10

(Chi8ral) Preparation of 4″,5-bis-O-tert-butyldimethyl-silyl-7-O-trimethylsilyl-23-nor-23-oxa-24-(R)-methyl-25-des-2-butyl-25-(R)-methyl-22-hydroxy-ivermectin (IVa.5)

250 mg Aldehyde-acid III (205 μmol) was placed in 1 mL methylene chloride at room temperature to which was added 250 mL (R,R)-trans-2,3-butanediol followed by 50 mg p-toluenesulfonic acid (290 μmol). After 15 min, the reaction was poured into 10 mL saturated NaHCO$_3$, extracted with methylene chloride and dried (MgSO$_4$). The solution was filtered and 193 mg IVa.5 (82%) was obtained in pure form by chromatography on silica gel using 85:15 hexanes: acetone as eluant.

EXAMPLE 11

Preparation of 4″,5-bis-O-tert-butyldimethylsilyl-7-O-trimethylsilyl-23-nor-23-oxa-24-tert-butyl-25-des-2-butyl-ivermectin (IVa.6) and 4″,5-bis-O-tert-butyldimethylsilyl-7-O-trimethylsilyl-23-nor-23-oxa-24-desmethyl-25-des-2-butyl-25-tert-butyl-ivermectin (IVa.6)

500 mg Aldehyde-acid III (410 μmol) was placed in 2 mL methylene chloride at room temperature to which was added 500 mg 3,3-dimethyl-1,2-butanediol (4.23 mmol) followed by 100 mg p-toluenesulfonic acid (581 μmol). After 15 min, the reaction was poured into 10 mL saturated NaHCO$_3$, extracted with methylene chloride and dried (MgSO$_4$). The solution was filtered, the product concentrated under reduced pressure and pure IVa.6 and IVb.6 (381 mg, 79%) were obtained as a 1:1 mixture after flash chromatography on silica gel using 3:1 hexanes:ethyl acetate as eluant.

EXAMPLE 12

Preparation of 4″,5-bis-O-tert-butyldimethylsilyl-7-O-trimethylsilyl-23-nor-23-oxa-24-(4-methylphenyl)-25-des-2-butyl-22-hydroxy-ivermectin (IVa.7) and 4″,5-bis-O-tert-butyldimethylsilyl-7-O-trimethylsilyl-23-nor-23-oxa-24-desmethyl-25-des-2-butyl-25-(4-methylphenyl)-22-hydroxy-ivermectin (IVb.7)

500 mg Aldehyde-acid III (410 μmol) was placed in 2 mL methylene chloride at room temperature to which was added 560 mg 1-[(4-Methyl)phenyl]-1,2-ethanediol (3.68 mmol) and 100 mg p-toluenesulfonic saturated NaHCO$_3$, extracted with methylene chloride and dried (MgSO$_4$). The solution was filtered, concentrated under reduced pressure and purified by flash chromatography on silica gel using 7:3:1 hexanes:ethyl acetate:methyl-tert-butyl ether as eluant. Product Va.1 was obtained in quantitative yield and the individual isomeric acetates were obtained in pure form in the following yields: Isomer A, 70 mg; Isomer B, 150 mg; Isomer C, 160 mg.

EXAMPLE 15

Preparation of 4″,5-bis-O-tert-butyldimethylsilyl-7-O-trimethylsilyl-23-nor-23-oxa-24-desmethyl-25-des-2-butyl-22-chloro-ivermectin (Va.2)

145 mg Alcohol IVa.1 (129 μmol) was placed in 2 mL methylene chloride at 0° C. to which was added 45 μL diisopropylethylamine (250 μmol) followed by 50 mg (C$_6$H$_5$)$_3$PCl$_2$ (150 μmol). The solution was warmed to room temperature and stirred for 30 min. Additional diisopropylethylamine (250 μmol) and (C$_6$H$_5$)$_3$PCl$_2$ (150 μmol) was then added and the solution was stirred for an additional 20 min. Without workup, the solution was filtered through a 4.0 cm pad of silica gel with 2:1 hexanes:ethyl acetate to remove polar impurities and the solution was concentrated under reduced pressure to yield 89 mg (61%) Va.2 as a pale yellow powder. acid (581 μmol). After 10 min, 1 mL triethylamine was added to the solution and the crude was purified without workup on silica gel using 1:1 hexanes:ethyl acetate as eluant to yield 272 mg IVa.7 (55%) and 192 mg IVb.7 (39%).

EXAMPLE 13

Preparation of 4″,5-bis-O-tert-butyldimethylsilyl-7-O-trimethylsilyl-23-nor-23-oxa-24,25-trans-cyclohexyl-25-des-2-butyl-ivermectin (IVa.8)

500 mg Aldehyde-acid III (410 μmol) was placed in 2 mL methylene chloride at room temperature to which was added 500 mg trans-1,2-cyclohexanediol (4.31 mmol) followed by 100 mg p-toluenesulfonic acid (581 μmol). After 15 min, the reaction was poured into 10 mL saturated NaHCO$_3$, extracted with methylene chloride and dried (MgSO$_4$). The solution was filtered, the product concentrated under reduced pressure and pure IVa.8 (419 mg, 87%) was obtained after flash chromatography on silica gel using 3:1 hexanes:ethyl acetate as eluant.

EXAMPLE 14

Preparation of 4″,5-bis-O-tert-butyldimethylsilyl-7-O-trimethylsilyl-23-nor-23-oxa-24-desmethyl-25-des-2-butyl-22-acetoxy-ivermectin (Va.1)

350 mg Alcohol IVa.1 (311 μmol) was dissolved in 5 mL methylene chloride at 0° C. to which was added sequentially 250 μL pyridine, 10 mg 4-dimethylaminopyridine and 150 μL acetic anhydride. After 15 min at 0° C., the reaction was poured into

EXAMPLE 16

Preparation of
4″,5-bis-O-tert-butyldimethylsilyl-7-O-trimethylsilyl-23-nor-23-oxa-24-methyl-25-des-2-butyl-22-chloro-ivermectin (Va.3) and
4″,5-bis-O-tert-butyldimethylsilyl-7-O-trimethylsilyl-23-nor-23-oxa-24-desmethyl-25-des-2-butyl-25-methyl-22-chloro-ivermectin (Vb.3)

347 mg Alcohol IVa.2 and IVb.2 (1:1 mixture) (305 $\mu$mol) was placed in 4 mL methylene chloride at 0° C. to which was added 268 $\mu$L diisopropylethylamine (1.5 mmol). To this was added 406 mg $(C_6H_5)_3PCl_2$ (1.22 mmol). After 5 min at 0° C. and 30 min at room temperature, the solution was poured into ice water and extracted with methylene chloride and dried (MgSO$_4$). The solution was filtered and concentrated under reduced pressure. Flash chromatography on silica gel yielded 318 mg (90%) pure product Va.3 and Vb.3 as a 1:1 mixture.

EXAMPLE 17

Preparation of
4″,5-bis-O-tert-butyldimethylsilyl-7-O-trimethylsilyl-23-nor-23-oxa-24-(4-methyl)phenyl-25-des-2-butyl-22-chloro-ivermectin (Va.4)

192 mg Alcohol IVa.7 (158 $\mu$mol) was dissolved in 4 mL methylene chloride at 0° C. to which was added 141 $\mu$L diisopropylethylamine (790 $\mu$mol) followed by 158 mg Ph$_3$PCl$_2$ (475 $\mu$mol). After 5 min at 0° C. and 30 min at room temperature, the crude was purified without workup by flash chromatography on silica gel using 3:1 hexanes:ethyl acetate as eluant to yield 107 mg Va.4 (55%) as a pale yellow powder.

EXAMPLE 18

(Racemic) Preparation of
4″,5-bis-O-tert-butyldimethylsilyl-7-O-trimethylsilyl-23-nor-23-oxa-24-methyl-25-des-2-butyl-25-methyl-22-pentafluorphenylthionocarbonate-ivermectin (Va.5)

50 mg Alcohol IVa.4 (43 $\mu$mol) was placed in 1 mL methylene chloride at 0° C. To this was added 60 $\mu$L pyridine (750 $\mu$mol) and 3 mg 4-dimethylaminopyridine followed by 30 $\mu$L pentafluorophenylthionochloroformate (195 $\mu$mol). After 30 min at 0° C., the crude was purified without workup by flash chromatography on silica gel using 85:15 hexanes:acetone as eluant to yield 36 mg Va.5 (61%) as a pale yellow powder.

EXAMPLE 19

(Racemic) Preparation of
4″,5-bis-O-tert-butyldimethylsilyl-7-O-trimethylsilyl-23-nor-23-oxa-24-methyl-25-des-2-butyl-25-methyl-22-bromo-ivermectin (Va.6)

50 mg Alcohol IVa.4 (43 $\mu$mol) was dissolved in 1 mL methylene chloride at 0° C. to which was added 22 mg $(C_6H_5)_3PBr_2$ (52 $\mu$mol) followed by 12 $\mu$L triethylamine (86 $\mu$mol). After 10 min at 0° C. and 15 min at room temperature, the crude was purified without workup on silica gel using 85:15 hexanes:acetone as eluant to yield 39 mg Va.8 (76%) as a pale yellow solid.

EXAMPLE 20

(Racemic) Preparation of
4″,5-bis-O-tert-butyldimethylsilyl-7-O-trimethylsilyl-23-nor-23-oxa-24-methyl-25-des-2-butyl-25-methyl-22-phenylseleno-ivermectin (Va.7)

50 mg Alcohol IVa.4 (43 $\mu$mol) was placed in 1 mL methylene chloride at room temperature to which was added 39 $\mu$L tri-n-butyl phosphine (156 $\mu$mol) and 48 mg N-phenylselenophthalamide (156 $\mu$mol). After 2 hrs at room temperature, the crude was purified without workup on silica gel using 85:15 hexanes:ethyl acetate as eluant to yield 33 mg Va.7 (59%) as a pale yellow solid.

EXAMPLE 21

Preparation of
4″,5-bis-O-tert-butyldimethylsilyl-7-O-trimethylsilyl-23-nor-23-oxa-24-methyl-25-des-2-butyl-22-bromo-ivermectin (Va.8) and
4″,5-bis-O-tert-butyldimethylsilyl-7-O-trimethylsilyl-23-nor-23-oxa-24-desmethyl-25-des-2-butyl-25-methyl-22-bromo-ivermectin (Vb.8)

177 mg Alcohol IVa.2 and IVb.2 (154 $\mu$mol) was placed in 3 mL methylene chloride at 0° C. To this was added 520 mg $(C_6H_5)_3PBr_2$ (1.23 mmol) followed by 224 $\mu$L triethylamine (1.60 mmol). The solution was warmed to room temperature. After 1 hr at room temperature, the solution was purified without workup on silica gel using 85:15 hexanes:acetone as eluant to yield 106 mg (57%) Va.8 and Vb.8 as a pale yellow oil.

EXAMPLE 22

(Chiral) Preparation of
4″,5-bis-O-tert-butyldimethylsilyl-7-O-trimethylsilyl-23-nor-23-oxa-24-methyl-25-des-2-butyl-25-methyl-22-acetoxy-ivermectin (Va.9)

35 mg Alcohol IVa.5 (30 $\mu$mol) was placed in 2 mL methylene chloride at room temperature to which was added sequentially 100 $\mu$L pyridine (1.26 mmol), 2 mg 4-dimethylaminopyridine and 50 $\mu$L acetic anhydride (490 $\mu$mol). After 10 min the solution was poured into 10 mL saturated NaHCO$_3$, extracted with ethyl acetate and dried (MgSO$_4$). The solution was filtered, concentrated under reduced pressure and purified by flash chromatography on silica gel using 2:1 hexanes:ethyl acetate as eluant to yield 29 mg (80%) acetate Va.9 as a colorless glass.

EXAMPLE 23

Preparation of
4″,5-bis-O-tert-butyldimethylsilyl-7-O-trimethylsilyl-23-nor-23-oxa-24-desmethyl-25-des-2-butyl-ivermectin (VIa.1)

100 mg Alcohol IVa.1 (89 $\mu$mol) was placed in 2 mL methylene chloride at 0° C. with 195 $\mu$L pyridine and 5 mg 4-dimethylaminopyridine. To this was added 142 $\mu$L pentafluorothionochloroformate. After 15 min, the solution was quenched with 10 mL ice water, extracted with methylene chloride and concentrated under reduced pressure. To this crude material was added 5 mL toluene, 5 mg azobis(2-methylpropionitrile) and 250 $\mu$L tri-n-butyl tin hydride. The solution was heated to 100° C. for 1 hour. Pure VIa.1 was obtained by flash chromatography on silica gel without workup 2:8 ethyl acetate:hexanes.

EXAMPLE 24

Preparation of
4'',5-bis-O-tert-butyldimethylsilyl-7-O-trimethylsilyl-23-nor-23-oxa-24-desmethyl-25-des-2-butyl-ivermectin (VIa.1)

89 mg Chloride Va.2 (78 μmol) was placed in 2.5 mL toluene with 0.5 mL tri-n-butyl tin hydride and 10 mg azobis(2-methylpropionitrile) and heated to 100° C. for 30 min. The crude was purified on silica gel using 3:1 hexanes:ethyl acetate without a workup to yield 74 mg VIa.1 (86%) as a white powder.

EXAMPLE 25

Preparation of
4'',5-bis-O-tert-butyldimethylsilyl-7-O-trimethylsilyl-23-nor-23-oxa-24-methyl-25-des-2-butyl-ivermectin (VIa.2) and
4'',5-bis-O-tert-butyldimethylsilyl-7-O-trimethylsilyl-23-nor-23-oxa-24-desmethyl-25-des-2-butyl-25-methyl-ivermectin (VIb.2)

318 mg Chloride Va.2 and Vb.2 (127 μmol) was placed in 2 mL toluene with 2 mL tri-n-butyl tin hydride and 5 mg azobis(2-methylpropionitrile) and heated to 100° C. for 15 min. The crude was purified without workup by flash chromatography on silica gel using 3:1 hexanes:ethyl acetate as eluant yielding 244 mg VIa.2 and VIb.2 (79%) as a white powder. The individual isomers could be separated at this juncture by preparative thin layer chromatography.

EXAMPLE 26

Preparation of
4'',5-bis-O-tert-butyldimethylsilyl-7-O-trimethylsilyl-23-nor-23-oxa-24-methyl-25-des-2-butyl-ivermectin (VIa.2) and
4'',5-bis-O-tert-butyldimethylsilyl-7-O-trimethylsilyl-23-nor-23-oxa-24-desmethyl-25-des-2-butyl-25-methyl-ivermectin (VIb.2)

106 mg Bromide Va.8 and Vb.8 (87 μmol) was placed in 2 mL toluene with 1 mL nBu₃SnH and 5 mg azobis(2-methylpropionitrile) and heated to 100° C. for 15 min. The crude was purified without workup by flash chromatography on silica gel using 9:1 hexanes:acetone as eluant to yield 82 mg (83%) VIa.2 and VIb.2 as a 1:1 mixture.

EXAMPLE 27

(Racemic) Preparation of
4'',5-bis-O-tert-butyldimethylsilyl-7-O-trimethylsilyl-23-nor-23-oxa-24-methyl-25-des-2-butyl-25-methyl-ivermectin (VIa.5)

36 mg Pentafluorophenylthionocarbonate Va.5 (26 μmol) was placed in 1 mL tri-n-butyl tin hydride to which was added 5 mg azobis(2-methylpropionitrile) and heated to 100° C. for 15 min. The crude was purified without workup by flash chromatography on silica gel using first 85:15 hexanes:ethyl acetate then 85:15 hexanes:acetone as eluant to yield 19 mg VIa.5 (64%) as a white powder.

EXAMPLE 28

(Racemic) Preparation of
4'',5-bis-O-tert-butyldimethylsilyl-7-O-trimethylsilyl-23-nor-23-oxa-24-methyl-25-des-2-butyl-25-methyl-ivermectin (VIa.5)

39 mg Bromide Va.6 (32 μmol) was placed in 1 mL tri-n-butyl tin hydride with 5 mg azobis(2-methylpropionitrile) and heated to 100° C. for 15 min. The crude was purified without workup by flash chromatography on silica gel using first 9:1 hexanes:ethyl acetate then 8:2 hexanes:ethyl acetate as eluant to yield 32 mg VIa.5 (89%) as a white powder.

EXAMPLE 29

(Racemic) Preparation of
4'',5-bis-O-tert-butyldimethylsilyl-7-O-trimethylsilyl-23-nor-23-oxa-24-methyl-25-des-2-butyl-25-methyl-ivermectin (VIa.5)

33 mg Phenylselenide Va.7 (26 μmol) was placed in 1 mL tri-n-butyl tin hydride with 5 mg azobis(2-methylpropionitrile) and heated to 100° C. for 15 min. The crude was purified without workup by flash chromatography on silica gel using first 9:1 hexanes:ethyl acetate then 8:2 hexanes:ethyl acetates eluant to yield 27 mg VIa.5 (92%) as a white powder.

EXAMPLE 30

(Chiral) Preparation of
4'',5-bis-O-tert-butyldimethylsilyl-7-O-trimethylsilyl-23-nor-23-oxa-24-methyl-25-des-2-butyl-25-methyl-ivermectin (VIa.6)

153 mg Alcohol IVa.5 (133 μmol) was dissolved in 3 mL toluene at 0° C. 133 mL Oxalyl chloride (266 μmol, 2M in CH₂Cl₂) was added followed by 1 drop dimethylformamide. After 15 min the solution was concentrated under reduced pressure at ambient temperature. To the crude product was added 2 mL toluene, 2 mL tri-n-butyl tin hydride and 5 mg azobis(2-methylpropionitrile) and the solution was heated to 100° C. for 15 min. Pure VIa.6 (119 mg, 78%) by flash chromatography without workup on silica gel using 3:1 hexanes:ethyl acetate as eluant.

EXAMPLE 31

(Chiral) Preparation of
4'',5-bis-O-tert-butyldimethylsilyl-7-O-trimethylsilyl-23-nor-23-oxa-24-methyl-25-des-2-butyl-25-methyl-ivermectin (VIa.6)

14 mg Acetate Va.9 (12 μmol) was dissolved in 1 mL methylene chloride to which was added 10 μL triethyl silane (62 μmol) and the solution cooled to −78° C. 1 μL freshly distilled boron trifluoridemethyl etherate was added and the reaction stirred at −78° C. for 5 min then warmed to 0° C. over 15 min. The reaction was quenched with 2 mL saturated NaHCO₃, extracted with ethyl acetate and dried (MgSO₄). The solution was filtered, concentrated under reduced pressure and purified by preparative thin layer chromatography (1000 micron silica gel plates, 8:2 hexanes:acetone as eluant) to yield 5 mg pure VIa.6 (36%) as a white powder.

EXAMPLE 32

Preparation of
23-nor-23-oxa-24-desmethyl-25-des-2-butyl-ivermectin
(VIa.1a)

74 mg Tris-silyl VIa.1 (67 μmol) was dissolved in 4 mL tetrahydrofuran at room temperature to which was added 1 mL HF.pyridine solution (25 g HF.pyridine, 10 mL pyridine, 25 mL tetrahydrofuran). The solution was stirred for 2 days and then poured into 40 mL 1:1 water:ether. The layers were separated and neutralized separately with saturated NaHCO$_3$. The aqueous layers were pooled and extracted with ether. The organic layers were combined and dried (MgSO$_4$). The MgSO$_4$ was filtered off, the crude concentrated under reduced pressure and 40 mg (75%) pure VIa.1a was obtained as a white powder by flash chromatography on silica gel using 3:1 ethyl acetate:hexanes as eluant.

EXAMPLE 33

Preparation of
23-nor-23-oxa-24-methyl-25-des-2-butyl-ivermectin and
23-nor-23-oxa-24-desmethyl-25-des-2-butyl-25-methyl-ivermectin 82 mg Tris-silyl VIa.2 and VIb.2 (72 μmol) was dissolved in 3 mL tetrahydrofuran at room temperature to which was added 1 mL HF.pyridine solution (25 g HF.pyridine, 10 mL pyridine, 25 mL tetrahydrofuran). The solution was stirred for 2 days and then poured into 40 mL 1:1 water:ether. The layers were separated and neutralized separately with saturated NaHCO$_3$. The aqueous layers were pooled and extracted with ether. The organic layers were combined and dried (MgSO$_4$). The solution was filtered, the crude concentrated under reduced pressure and 34 mg (57%) pure and 24-methyl and 25-methyl product were obtained by flash chromatography on silica gel using 3:1 ethyl acetate:hexanes as eluant.

EXAMPLE 34

(Chiral) Preparation of
23-nor-23-oxa-24-methyl-25-des-2-butyl-25-methyl-ivermectin 61 mg Tris-silyl ether VIa.6 (54 μmol) was dissolved in 3 mL tetrahydrofuran at room temperature to which was added 1 mL HF.pyridine solution (25 g HF.pyridine, 10 mL pyridine, 25 mL tetrahydrofuran). The solution was stirred for 2 days and then poured into 40 mL 1:1 water:ether. The layers were separated and neutralized separately with saturated NaHCO$_3$. The aqueous layers were pooled and extracted with ether. The organic layers were combined and dried (MgSO$_4$). The solution was filtered, the crude concentrated under reduced pressure and 34 mg (61%) pure chiral product was obtained by flash chromatography on silica gel using 3:1 ethyl acetate:hexanes as eluant.

EXAMPLE 35

Preparation of
23-nor-23-oxa-24-desmethyl-25-des-2-butyl-22-acetoxy-ivermectin (VIIa)

70 mg Tris-silyl acetate Va.1 (Isomer A, 60 μmoL) was dissolved in 4 mL tetrahydrofuran at room temperature to which was added 1 mL HF.pyridine solution (25 g HF.pyridine, 10 mL pyridine, 25 mL tetrahydrofuran). The solution was stirred for 2 days and then poured into 40 mL 1:1 water:ether. The layers were separated and neutralized separately with saturated NaHCO$_3$. The aqueous layers were pooled and extracted with ether. The organic layers were combined and dried (MgSO$_4$). The MgSO$_4$ was filtered off, the crude concentrated in vacuo and pure VIIa was obtained by flash chromatography on silica gel using 3:1 ethyl acetate:hexanes as eluant.

EXAMPLE 36

Preparation of
23-nor-23-oxa-24-desmethyl-25-des-2-butyl-22-acetoxy-ivermectin (VIIb)

150 mg Tris-silyl acetate Va.1 (Isomer B, 128 μmoL) was dissolved in 4 mL tetrahydrofuran at room temperature to which was added 1 mL HF.pyridine solution (25 g HF.pyridine, 10 mL pyridine, 25 mL tetrahydrofuran). The solution was stirred for 2 days and then poured into 40 mL 1:1 water:ether. The layers were separated and neutralized separately with saturated NaHCO$_3$. The aqueous layers were pooled and extracted with ether. The organic layers were combined and dried (MgSO$_4$). The MgSO$_4$ was filtered off, the crude concentrated in vacuo and pure VIIb was obtained by flash chromatography on silica gel using 3:1 ethyl acetate:hexanes as eluant.

EXAMPLE 37

Preparation of
23-nor-23-oxa-24-desmethyl-25-des-2-butyl-22-acetoxy-ivermectin (VIIc)

150 mg Tris-silyl acetate Va.1 (Isomer C, 128 μmoL) was dissolved in 4 mL tetrahydrofuran at room temperature to which was added 1 mL HF.pyridine solution (25 g HF.pyridine, 10 mL pyridine, 25 mL tetrahydrofuran). The solution was stirred for 2 days and then poured into 40 mL 1:1 water:ether. The layers were separated and neutralized separately with saturated NaHCO$_3$. The aqueous layers were pooled and extracted with ether. The organic layers were combined and dried (MgSO$_4$). The MgSO$_4$ was filtered off, the crude concentrated in vacuo and pure VIIc was obtained by flash chromatography on silica gel using 3:1 ethyl acetate:hexanes as eluant.

EXAMPLE 38

(Chiral) Preparation of
23-nor-23-oxa-24-methyl-25-des-2-butyl-25-methyl-ivermectin aglycone 75 mg Tris-silyl ether VIa.6 (66 μmol) was placed in 3 mL methanol containing 1% conc H$_2$SO$_4$ and stirred at room temperature for 48 hrs. The reaction was poured into 20 mL saturated NaHCO$_3$, extracted with ethyl acetate and dried (MgSO$_4$). The solution was filtered, concentrated under reduced pressure and purified by flash chromatography on silica gel using 3:1 ethyl acetate:hexanes as eluant to yield 29 mg (81%) of the chiral aglycone product as a white powder.

What is claimed is:

1. The compound having the formula:

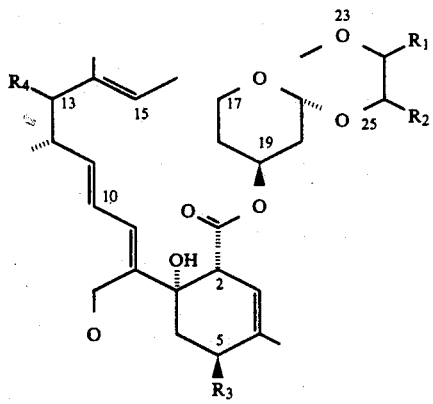

where
R₁ and R₂ are independently hydrogen, $C_1$–$C_{10}$ alkyl, $C_2$–$C_{10}$ alkenyl, $C_2$–$C_{10}$ alkynyl, $C_1$–$C_{10}$ alkoxy $C_1$–$C_{10}$ alkyl or $C_1$–$C_{10}$ alkylthio $C_1$–$C_{10}$ alkyl group; a $C_3$–$C_8$ cycloalkyl or $C_5$–$C_8$ cycloalkenyl group, either of which may optionally be substituted by methylene or from 1 to 3 of $C_1$–$C_4$ alkyl groups or halo atoms; phenyl, phenoxy, $C_1$–$C_{10}$ alkyl phenyl, $C_2$–$C_{10}$ alkenyl phenyl, $C_2$–$C_{10}$ alkynyl phenyl, substituted $C_1$–$C_{10}$ alkyl wherein the substituents independently are 1 to 3 of $C_1$–$C_5$ alkyl, $C_3$–$C_8$ cycloalkyl or substituted $C_1$–$C_{10}$ alkyl wherein the substituents are independently 1 to 3 of hydroxy, halogen, cyano, $C_1$–$C_5$ alkyl thio, $C_1$–$C_5$ alkyl sulfinyl, $C_1$–$C_5$ alkyl sulfonyl, amino, $C_1$–$C_5$ mono or dialkyl amino, $C_1$–$C_5$ alkanoyl amino or $C_1$–$C_5$ alkanoylthio;

R₃ is hydroxy, $C_1$–$C_5$-alkoxy, hydroximino or —O—$C_1$–$C_5$ alkyl-hydroximino;

R₄ is hydrogen, halogen, hydroxy, $C_1$–$C_5$ alkanoyloxy, ($C_1$–$C_5$-alkoxy)ₙ where n is 1–4,

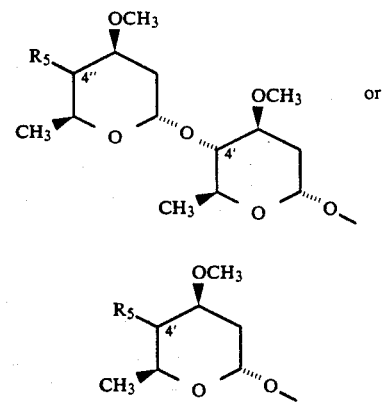

where R₅ is hydroxy, oxo, ($C_1$–$C_5$ alkyl)ₘ amino, $C_1$–$C_5$ alkanoyl amino, ($C_1$–$C_5$ alkyl)($C_1$–$C_5$ alkanoyl) amino, $C_1$–$C_5$ alkyl-S(O)ₘ, hydroxy substituted $C_1$–$C_5$ alkyl S(O)ₘ, where m is 0, 1 or 2 or ($C_1$–$C_5$-alkoxy)ₙ where n=1–4.

2. A compound of claim 1 where:
R₁ and R₂ are independently hydrogen, $C_1$–$C_5$ alkyl, $C_2$–$C_5$ alkenyl, $C_1$–$C_5$ alkoxy, a $C_5$–$C_6$ cycloalkyl or $C_5$–$C_6$ cycloalkenyl group, either of which may optionally be substituted by methylene or from 1 to 3 of $C_1$–$C_4$ alkyl groups; phenyl, phenoxy, $C_{1-5}$ alkyl phenyl, $C_2$–$C_5$ alkenyl phenyl, substituted $C_1$–$C_5$ alkyl wherein the substituents independently are 1 to 3 of $C_1$–$C_3$ alkyl, $C_1$–$C_3$ alkyl thio, $C_1$–$C_3$ alkyl sulfinyl, $C_1$–$C_3$ alkyl sulfonyl, R₃ is hydroxy, $C_1$–$C_3$-alkoxy, $C_1$–$C_3$-alkanoyloxy hydroximino or —O—$C_1$–$C_5$ alkyl-hydroximino;

R₄ is hydrogen, halogen, hydroxy, $C_1$–$C_3$-alkanoyloxy, ($C_1$–$C_3$ alkoxy)ₙ, where n is 1–2,

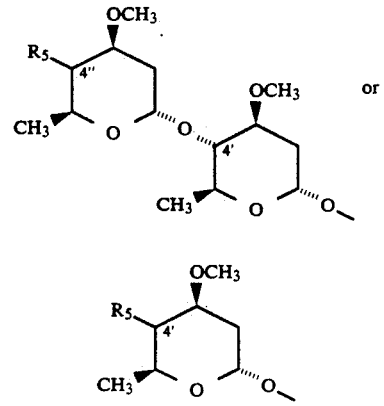

where R₅ is hydroxy, $C_1$–$C_3$ alkyl amino, $C_1$–$C_3$ alkanoyl amino, ($C_1$–$C_3$ alkyl)($C_1$–$C_3$ alkanoyl) amino, $C_1$–$C_3$ alkyl-S(O)ₘ, hydroxy substituted $C_1$–$C_3$ alkyl S(O)ₘ, where m is 0, 1 or 2 or ($C_1$–$C_3$-alkoxy)ₙ where n=1–4.

3. A compound of claim 2 where:
R₁ is hydrogen, $C_1$–$C_4$-alkyl;
R₂ is hydrogen, $C_1$–$C_5$ alkyl, $C_2$–$C_5$ alkenyl, $C_1$–$C_5$ alkoxy, a $C_5$–$C_6$ cycloalkyl or $C_5$–$C_6$ cycloalkenyl group, phenyl, substituted $C_1$–$C_5$ alkyl wherein the substituents independently are 1 to 3 of $C_1$–$C_3$ alkyl;
R₃ is hydroxy, hydroximino or —O—$C_1$–$C_2$ alkyl-hydroximino;
R₄ is hydrogen, halogen, hydroxy, $C_1$–$C_2$-alkanoyloxy, ($C_1$–$C_3$ alkoxy)ₙ where n is 1–2,

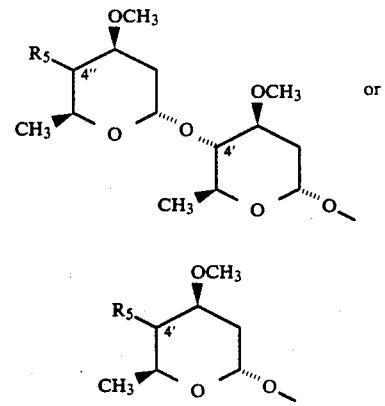

where R₅ is hydroxy, $C_1$–$C_2$ alkyl amino, $C_1$–$C_2$ alkanoyl amino, ($C_1$–$C_2$ alkyl)($C_1$–$C_2$ alkanoyl) amino, $C_1$–$C_2$ alkyl-S(O)ₘ, hydroxy substituted $C_1$–$C_2$ alkyl S(O)ₘ, where m is 0, 1 or 2.

4. A compound of claim 1 which is:
23-nor-23-oxa-24-desmethyl-25-desbutyl-24-phenyl ivermectin B1;

23-nor-23-oxa-24-desmethyl-25-desbutyl-25-phenyl ivermectin B1;
23-nor-23-oxa-24-desmethyl-25-desbutyl-24-(4-methyl)-phenyl ivermectin B1;
23-nor-23-oxa-24-desmethyl-25-desbutyl-25-(4-methyl)-phenyl ivermectin B1;
23-nor-23-oxa-24-desmethyl-25-desbutyl-24-methyl ivermectin B1;
23-nor-23-oxa-24-desmethyl-25-desbutyl-25-methyl ivermectin B1;
23-nor-23-oxa-24-desmethyl-25-desbutyl-24-t-butyl ivermectin B1;
23-nor-23-oxa-24-desmethyl-25-desbutyl-25-t-butyl ivermectin B1;
23-nor-23-oxa-24-desmethyl-25-desbutyl-24-cyclohexyl ivermectin B1;
23-nor-23-oxa-24-desmethyl-25-desbutyl-25-cyclohexyl ivermectin B1;
23-nor-23-oxa-24-methyl-25-desbutyl-25-methyl ivermectin B1;
23-nor-23-oxa-24-desmethyl-25-desbutyl-24,25-cyclohexyl ivermectin B1.
23-nor-23-oxa-24-desmethyl-ivermectin B1;
23-nor-23-oxa-24-desmethyl-25-desbutyl-25-(2-butyl) ivermectin B1;
23-nor-23-oxa-24-desmethyl-25-desbutyl-25-isopropyl-ivermectin B1;
23-nor-23-oxa-24-desmethyl-25-desbutyl-25-ethyl-ivermectin B1;
23-nor-23-oxa-24-desmethyl-25-desbutyl-25-[2-(4-methylpent-2-enyl)]ivermectin B1;
23-nor-23-oxa-24-desmethyl-5-ketoxime-ivermectin B1;
23-nor-23-oxa-24-desmethyl-4''-epi-amino-4''deoxy-ivermectin B1;
23-nor-23-oxa-24-desmethyl-25-desbutyl-4''-epi-acetyl(methyl)amino-4''-deoxy-ivermectin B1;
23-nor-23-oxa-24-desmethyl-25-desbutyl-25-cyclohexyl ivermectin B1 aglycone;
23-nor-23-oxa-24-methyl-25-desbutyl-25-methyl ivermectin B1 aglycone;
23-nor-23-oxa-24-desmethyl-25-desbutyl-25-methyl-13-O-methoxymethyl-ivermectin B1 aglycone.
23-nor-23-oxa-24-desmethyl-25-desbutyl-25-phenyl-13-deoxy-13-chloro-ivermectin B1 aglycone;
23-nor-23-oxa-24-desmethyl-25-desbutyl-25-phenyl-13-deoxy-13-fluoro-ivermectin B1 aglycone;
23-nor-23-oxa-24-methyl-25-desbutyl-25-isopropyl-4''-deoxy-4''-(2-acetylaminoethyl)thio-ivermectin B1;
23-nor-23-oxa-24-desmethyl-25-desbutyl-25-isopropyl-4''-deoxy-4''-(2-acetylaminoethyl)sulfonyl-ivermectin B1.

5. A composition useful for the treatment of parasitic infections in animals or parasitic infestations of plants which comprises an inert carrier and a compound of claim 1.

6. A method for the treatment of parasitic infections of animal which comprises administering to an animal infected with such parasites a compound of claim 1.

7. A method for the treatment of parasitic infestations of plants which comprises applying to such plant or the soil in which it grows, an effective amount of a compound of claim 1.

8. A method for the treatment of premises infected with parasites which comprises applying to such premises an effective amount of a compound of claim 1.

* * * * *

UNITED STATES PATENT AND TRADEMARK OFFICE
CERTIFICATE OF CORRECTION

PATENT NO. : 5,244,879

DATED : September 14, 1993

INVENTOR(S) : Peter T. Meinke and Helmut Mrozik

It is certified that error appears in the above-indentified patent and that said Letters Patent is hereby corrected as shown below:

In column 1, between lines 35 and 50, delete the structural formula and replace the structural formula with the following:

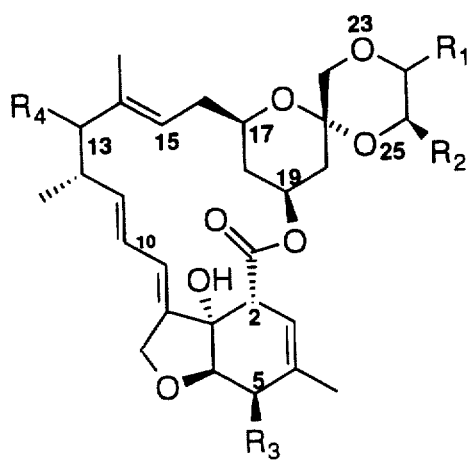

In column 5, at the top, delete the structures and replace with the following:

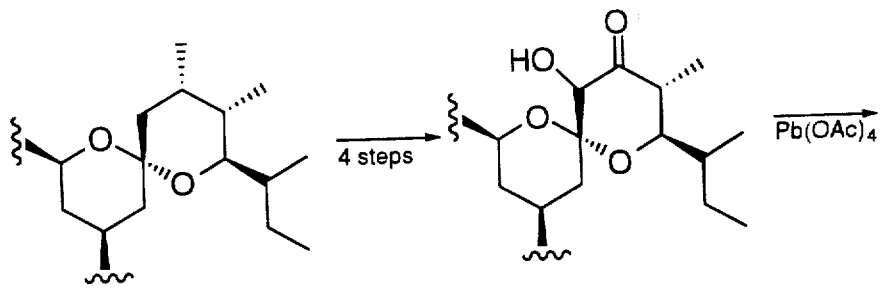

UNITED STATES PATENT AND TRADEMARK OFFICE
CERTIFICATE OF CORRECTION

PATENT NO. : 5,244,879

DATED : September 14, 1993

INVENTOR(S) : Peter T. Meinke and Helmut Mrozik

Page 2 of 2

It is certified that error appears in the above-indentified patent and that said Letters Patent is hereby corrected as shown below:

In claim 1, column 25, lines 1-17, delete the structural formula and replace the structural formula with the following:

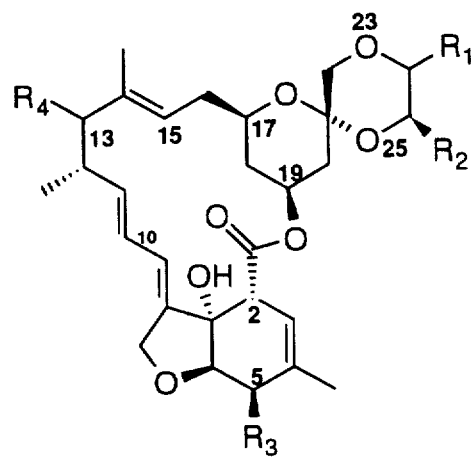

Signed and Sealed this

Twenty-ninth Day of March, 1994

Attest:

BRUCE LEHMAN

Attesting Officer

Commissioner of Patents and Trademarks